US005843479A

United States Patent [19]
Kelm et al.

[11] Patent Number: 5,843,479
[45] Date of Patent: Dec. 1, 1998

[54] BISACODYL DOSAGE FORM WITH MULTIPLE ENTERIC POLYMER COATINGS FOR COLONIC DELIVERY

[75] Inventors: Gary Robert Kelm, Cincinnati, Ohio; Koji Kondo; Akio Nakajima, both of Kobe, Japan

[73] Assignee: The Procter & Gamble Company, Cincinnati, Ohio

[21] Appl. No.: 728,945

[22] Filed: Oct. 11, 1996

Related U.S. Application Data

[63] Continuation-in-part of Ser. No. 442,914, May 17, 1995, Pat. No. 5,656,290, which is a continuation-in-part of Ser. No. 279,361, Jul. 22, 1994, abandoned, which is a continuation of Ser. No. 023,412, Feb. 26, 1993, abandoned.

[51] Int. Cl.$^6$ .............................. A61K 9/32; A61K 9/34; A61K 9/36
[52] U.S. Cl. .............................................................. 424/479
[58] Field of Search .................................... 424/480, 468, 424/481, 482, 479

[56] References Cited

U.S. PATENT DOCUMENTS

| | | | |
|---|---|---|---|
| 2,764,590 | 9/1956 | Kottler et al. . | |
| 3,431,338 | 3/1969 | Munzel | 424/21 |
| 4,432,966 | 2/1984 | Zeitoun et al. | 424/21 |
| 4,816,259 | 3/1989 | Matthews et al. | 424/463 |
| 4,822,629 | 4/1989 | Pong | 424/480 |
| 4,834,985 | 5/1989 | Elger at al. | 424/488 |
| 4,910,021 | 3/1990 | Davis et al. | 424/456 |
| 4,952,402 | 8/1990 | Sparks et al. | 424/419 |
| 5,068,110 | 11/1991 | Fawzi et al. | 424/461 |
| 5,171,580 | 12/1992 | Iamartino et al. | 424/490 |
| 5,217,720 | 6/1993 | Sekigawa et al. | 424/480 |
| 5,283,064 | 2/1994 | Suzuki et al. | 424/451 |
| 5,330,759 | 7/1994 | Pagay et al. | 424/462 |
| 5,525,634 | 6/1996 | Sintov et al. | 514/777 |
| 5,541,170 | 7/1996 | Rhodes et al. | 514/166 |
| 5,541,171 | 7/1996 | Rhodes et al. | 514/166 |

FOREIGN PATENT DOCUMENTS

| | | | |
|---|---|---|---|
| 839-625 | 7/1976 | Belgium . | |
| 0225189 | 11/1986 | European Pat. Off. | A61K 9/48 |
| 0251459 | 7/1988 | European Pat. Off. | A61K 9/22 |
| 0313845 | 9/1988 | European Pat. Off. | A61K 9/32 |
| 3133-625 | 11/1978 | Japan | A61K 9/36 |
| 57-099521 | 6/1982 | Japan | A61K 31/44 |
| 63-20409 | 6/1982 | Japan . | |
| 61-221117 | 10/1986 | Japan . | |
| 63-258815-A | 10/1988 | Japan | A61K 31/44 |
| 01117826-A | 5/1989 | Japan | A61K 9/48 |
| 59-139317-A | 8/1994 | Japan | A61K 9/64 |
| 59-193816 | 11/1994 | Japan . | |
| 2151921 | 7/1985 | United Kingdom | A61K 9/26 |
| WO 83/00435 | 2/1983 | WIPO | A61K 9/32 |
| WO 94/18973 | 9/1994 | WIPO | A61K 31/44 |

OTHER PUBLICATIONS

Schmidt, P.C., "The MiniWiD–Coater: II. Comparison of Acid Resistance of Enteric–Coated Bisacodyl Pellets Coated With Different Polymers," Drug Development & Industrial Pharmacy, vol. 18, No. 18 (1992), pp. 1969–1979.

Luce, G. T., "Disintegration of tablets enteric coated with cellulose acetate phthalate," Pharm. Tech., vol. 2 (Oct. 1978), pp. 51–55.

Spitael, J., et al. "Enteric Coating using cellulose acetate phthalate", Manuf. Chem.; vol. 57, No. 8 (Aug. 1986), pp 35, 37.

Kane, Y. et al. "Technological evaluation of three enteric coating polymers. Part I. With an insoluble drug," Drug Dev. Ind. Pharm., vol. 19, No. 16 (1993), pp. 2011–2020.

Luce, G. T., "Disintegration of tablets enteric coated with CAP (cellulose acetate phthalate)," Manuf. Chem. Aerosol News, vol. 49, No. 50 (1978), pp. 50, 52, 67.

Preston, D.M., "Pelvic Motility and Response to Intraluminal Bisacodyl in Slow–Transit Constipation," Digestive Diseases & Sciences, vol. 30, No. 4 (1985), pp. 289–294.

Kamm, M.A. et al., "Dynamic scanning defines a colonic defect in severe idiopathic constipation," Gut, vol. 29 (1988), pp. 1085–1092.

Jauch, R. et al., "Bis–(p–hydroxyphenyl)–pyridyl–2–methane: The Common Laxative Principle of Bisacodyl and Sodium Picosulfate," Arzneim.–Forsch. (Drug Res.), vol. 25, No. 11 (1975), pp. 1796–1800.

Roth, W., "Translation of Pharmacokinetics and Laxative Effect of Bisacodyl After Administration of Various Dosage Forms," Arzneim.–Forsch./Drug Res., vol. 38(l), No. 4 (1988), pp. 570–574.

(List continued on next page.)

*Primary Examiner*—Peter F. Kulkosky
*Attorney, Agent, or Firm*—Betty J. Zea; John M. Howell; Jacobus C. Rasser

[57] ABSTRACT

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of rapidly dissolving bisacodyl incorporated into a compressed, bi-convex tablet, with a maximum diameter of about 4 mm to about 10 mm;

b. a non-pH dependent smoothing coat applied to the tablet to provide a smooth tablet surface free from edges and sharp curves; and c. an enteric polymer coating material comprising at least one inner coating layer and only one outer coating layer;

wherein the rapidly dissolving bisacodyl is released at a point near the inlet to, or within the colon; each of the inner coating layer(s) is an enteric polymer that begins to dissolve in an aqueous media at a pH between about 5 to about 6.3; and the outer coating layer is an enteric polymer that begins to dissolve in an aqueous media at a pH between about 6.8 to about 7.2.

17 Claims, No Drawings

OTHER PUBLICATIONS

Leng–Peschlow, E., "Effects of Sennosides A+ B and Bisacodyl on Rat Large Intestine," Pharmacology, vol. 38 (1989), pp. 310–318.

Rasmussen, S., "Intestinal Absorption of Quinine from Enteric Coated Tablets," Acta Pharmacol. el Toxicol vol. 24 (1966) pp. 331–345.

U.S. application No. 08/442,914, Kelm et al., filed May 17, 1995, Co–pending P&G Case 5672, "Bisacodyl Dosage Form with Multiple Enteric Polymer Coatings for Colonic Delivery".

U.S. application No. 08/442,920, Kelm et al., filed May 17, 1995, Co–pending P&G Case 5674, "Pharmaceutical Dosage Forms with Multiple Enteric Coatings for Colonic Delivery".

BISACODYL DOSAGE FORM WITH MULTIPLE ENTERIC POLYMER COATINGS FOR COLONIC DELIVERY

This is a continuation-in-part of application Ser. No. 08/442,914, filed on May 17, 1995, now U.S. Pat. No. 5,556,290 which is a continuation-in-part of application Ser. No. 08/279,361, now abandoned filed on Jul. 22, 1994, which is a continuation of a Application of Ser. No. 08/023,412, filed now abandoned Feb. 26, 1993.

TECHNICAL FIELD

The present invention relates to novel unit dosage forms containing bisacodyl for colonic delivery to provide laxation in the colon.

BACKGROUND OF THE INVENTION

Bisacodyl, 4,4'-(2-pyridylmethylene)bisphenoldiacetate, is disclosed in the *Merck Index,* 11th ed. (1989), S. Budavari, ed., No. 1253, p. 193. Bisacodyl is an inactive prodrug that is hydrolyzed by intestinal brush border enzymes and colonic bacteria to desacetyl bisacodyl which is the active species. (R. Jauch, R. Hankwitz, K. Beschke, & H. Pelzer, "Bis-(p-hydroxyphenyl)-pyridyl-2-methane: The Common Laxative Principle of Bisacodyl and Sodium Picosulfate", *Arzneim.-Forsch./Drug Res.* 25 (11), 1796–1800, 1975). Contact of the desacetyl bisacodyl with the mucosa of the colon stimulates sensory nerve endings to produce increased propulsive peristaltic contractions of the colon which accelerate movement of contents through the colon. Both bisacodyl and desacetyl bisacodyl are poorly water soluble with absorption reported from both the small intestine and colon. Absorption from the small intestine may be greater than from the colon.

Delivery of suspensions or solutions of bisacodyl to the colon is known to result in laxation. (M. A. Kamm, J. E. Lennard-Jones, D. G. Thompson, R. Sobnack, N. W. Garvie, N, Granowska, "Dynamic Scanning Defines a Colonic Defect in Severe Idiopathic Constipation", *Gut,* Vol. 29, pp 1085–1092, 1988; D. M. Preston, J. E. Lennard-Jones, "Pelvic Motility and Response to Intraluminal Bisacodyl in Slow-Transit Constipation", *Digestive Diseases and Sciences,* Vol. 30, No 4, pp 289–294, 1985; E. Leng-Peschlow, "Effect of Sennosides A+B and Bisacodyl on Rat Large Intestine", *Pharmacology,* Vol. 38, pp 310–318, 1988).

A dosage form that truly delivers a concentrated form of bisacodyl to the colon, with minimum absorption occurring in the small intestine, would be desirable for several reasons. Since desacetyl bisacodyl acts upon contact with the lumenal mucosa of the colon, its laxative effect is dependent upon generation of sufficient levels of the drug in the lumen of the colon. However, it has been determined that secondary diarrhea and/or repeat bowel movements associated with peroral administration of bisacodyl is at least partially due to the fact that absorbed desacetyl bisacodyl is partially excreted in the bile as the glucuronide conjugate which can be subsequently cleaved by colonic bacteria releasing desacetyl bisacodyl. Therefore, it is desirable to minimize absorption of desacetyl bisacodyl from the small intestine and colon while achieving therapeutically effective levels of the drug in the lumen of the colon. Lower doses of bisacodyl can be used if bisacodyl is delivered in an undiluted, rapidly dissolving form, to its site of activity in the colon. Low doses will provide laxation efficacy with minimal side effects such as repeat bowel movements, cramping, and secondary diarrhea.

Release of bisacodyl in the colon as a preferred mode of delivery of the drug in order to minimize systemic absorption of bisacodyl is disclosed in W. Roth, K. Beschke, "Pharmnacokinetics and Laxative Effect of Bisacodyl after Administration of Various Dosage Forms", *Arzneim.— Forsch./Drug Res.,* Vol. 38(I), No. 4 (1988), pp. 570–574.

Commercially-available bisacodyl compositions are typically coated with a low level of an enteric polymer or combination of polymers. An example of such a commercially available product is Dulcolax® (Boehringer Ingelheim Pharmaceuticals, Ridgefield, Conn). (See also, enteric coated bisacodyl tablets indicated for the relief of constipation in the *Physician's Desk Reference for Non Prescription Drugs,* 13th ed. (1992), p. 550.) Dulcolax® is typically coated with a low level of cellulose acetate phthalate, and each tablet has about 5 mg of bisacodyl. The recommended dose is from 1 to 3 tablets (from 5 to 15 mg of bisacodyl). Another example is Colac® (Procter & Gamble Pharmaceuticals) which is coated with a low level of a 50/50 mixture of Eudragit®S and Eudragit® L, with the same recommended dosing as Dulcolox®. These bisacodyl formulations are formulated in such a way that they are not rapidly dissolving once the bisacodyl reaches the colon. In addition the level of coating is much less than the amount required by the present invention.

Colonic delivery dosage forms are known in the art. For example, U.S. Pat. No. 5,171,580, issued Dec. 15, 1992, Boehringer Ingelheim Italia, teaches a preparation for delivery in the large intestine and especially the colon, comprising an active containing core coated with three protection layers of coatings having different solubilities. The inner layer is Eudragit® S, with a coating thickness of about 40–120 microns, the intermediate coating layer is a swellable polymer with a coating thickness of about 40–120 microns, and the outer layer is cellulose acetate phthalate, hydroxypropylmethyl cellulose phthalate, polyvinyl acetate phthalate, hydroxyethyl cellulose phthalate, cellulose acetate tetrahydrophthalate, or Eudragit®L. In the dosage forms of the present invention Eudragit®S is only used as an outer layer.

U.S. Pat. No. 4,910,021, issued on Mar. 20, 1990, Scherer Corp., teaches a targeted delivery system wherein the composition comprises a hard or soft gelatin capsule containing an active ingredient such as insulin and an absorption promoter, which is coated with a film forming composition being sufficiently soluble at a pH above 7 as to be capable of permitting the erosion or dissolution of said capsule. The film forming composition is preferably a mixture of Eudragit®L, Eudragit® RS, and Eudragit® S at specific ratios to provide solubility above a pH of 7.

U.S. Pat. No. 4,432,966, issued on Feb. 21, 1984, Roussel-UCLAF, teaches a compressed tablet with an active agent, coated with a first coating layer comprising a mixture of microcrystalline cellulose and lower alkyl ether of a cellulose film-forming organic polymer such as ethyl cellulose, and a second coating layer selected from cellulose acetylphthalate, hydroxypropyl methylcellulose phthalate, benzophenyl salicylate, cellulose acetosuccinate, copolymers of styrene and of maleic acid, formulated gelatin, salol, keratin, stearic acid, myristic acid, gluten, acrylic and methacrylic resins, and copolymers of maleic acid and phthalic acid derivatives.

In addition, the art also teaches that certain coating compositions are advantageous for ease of processing. For example, U.S. Pat. No. 5,330,759, issued Jul. 19, 1994, Sterling Winthrop, Inc., teaches soft capsules coated with an enteric coating comprising from about 1 to about 20 mg./cm² of 1:1 copolymer of methacrylic acid and methyl or ethyl acrylate or methyl ethyl methacrylate and a plasticizer. Glidants such as talc, to prevent agglomeration of the capsules, and a subcoating, to stiffen the capsules and thereby prevent distortion during coating, are not needed. This reference does not teach colonic delivery nor the importance of a smooth substrate surface without edges or sharp curves, and does not teach the specific multiple coating layers required by the present invention.

In addition, dosage forms with higher levels of coating are also known in the art. For example U.S. Pat. No. 5,068,110, issued on Nov. 26, 1991, Warner-Lambert Co., teaches dosage forms with a high level of enteric coating using aqueous systems in their manufacturer, such as Eudragit® L30D, Aquateric® (cellulose acetate phthalate) and Coateric® (polyvinyl acetate phthalate), for improved dissolution stability for storage under high stress conditions. The coating levels disclosed are from 14 mg/cm² to 24 mg/cm², of a single layer of one enteric polymer. These dosage forms are delivered to the small intestine as opposed to the colon.

In summary, colonic delivery of a peroral unit dosage form from which bisacodyl rapidly dissolves in the colon, will provide a higher in-situ concentration of the active compound for a more localized effect, permitting the use of lower doses, resulting in lower side effects. Therefore, a peroral dosage form which will preserve bisacodyl throughout the upper part of the gastrointestinal tract and thereafter rapidly release it in the colon, is desirable.

It is an object of the present invention to provide a dosage form of bisacodyl which provides laxation efficacy to patients without the occurrence of significant side effects such as substantial secondary diarrhea, repeat bowel movements and cramping.

It is a further object of the present invention to provide a colonic delivery dosage form of enteric coated bisacodyl which does not prematurely release bisacodyl in the upper gastrointestinal tract.

It is a further object of the present invention to provide laxation efficacy at substantially lower doses than is required with current peroral dosage forms of bisacodyl.

SUMMARY OF THE INVENTION

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of rapidly dissolving bisacodyl incorporated into a compressed, bi-convex tablet, with a maximum diameter of about 4 mm to about 10 mm;

b. a non-pH dependent smoothing coat applied to the tablet to provide a smooth tablet surface free from edges or sharp curves; and c. an enteric polymer coating material comprising at least one inner coating layer and only one outer coating layer;

wherein the rapidly dissolving bisacodyl is released at a point near the inlet to, or within the colon; each of the inner coating layer(s) is an enteric polymer that begins to dissolve in an aqueous media at a pH between about 5 to about 6.3; the outer coating layer is an enteric polymer that begins to dissolve in an aqueous media at a pH between about 6.8 to about 7.2; and wherein the incorporation of the bisacodyl into the dosage form is such that bisacodyl dissolves rapidly from the dosage form.

DETAILED DESCRIPTION OF THE INVENTION

It has been surprisingly discovered that laxation in rats (measured as acceleration of transit time through the colon and increase in output of fecal material) produced by delivery of bisacodyl to the colon, is a function of the dissolution rate (dose multiplied by intrinsic dissolution rate) of the administered drug, whereas side effects such as secondary episodes of diarrhea are a function of total administered dose. Thus, bisacodyl administered in the colon as a suspension of very fine, rapidly dissolving particles (essentially all particles less than 10 $\mu$m ), or in a solubilised form, for example an inclusion complex with hydroxypropyl-$\beta$-cyclodextrin, produces maximal laxation in rats at low total doses which do not evoke secondary episodes of diarrhea. In contrast, delivery to the colon of a suspension of more slowly dissolving forms of bisacodyl requires significantly higher doses to produce maximal laxation which also evoke secondary episodes of diarrhea. It has been further demonstrated that there is a linear relationship between cumulative bisacodyl dissolution and acceleration of colonic transit, a measure of laxative efficacy. Therefore, low doses of rapidly dissolving bisacodyl administered in the colon provide laxation efficacy equivalent to larger doses of more slowly dissolving bisacodyl, with reduced side effects.

Although not wishing to be bound by theory, it is believed that the elimination of secondary diarrhea of colonically delivered doses of rapidly dissolving bisacodyl is due to significantly reduced absorption and subsequent biliary recirculation of bisacodyl derived species. Reduced absorption is believed to be the result of colonic delivery (no absorption from the small intestine where the drug is therapeutically inactive), a lower dose, and the laxative effect of the drug which serves to evacuate unabsorbed drug from the colon.

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of rapidly dissolving bisacodyl incorporated into a compressed, bi-convex tablet, with a maximum diameter of about 4 mm to about 10 mm;

b. a non-pH dependent smoothing coat applied to the tablet to provide a smooth surface free from edges or sharp curves; and c. an enteric polymer coating material comprising at least one inner coating layer and only one outer coating layer;

wherein the rapidly dissolving bisacodyl is released at a point near the inlet to, or within the colon; each of the inner coating layer(s) is an enteric polymer that begins to dissolve in an aqueous media at a pH between about 5 to about 6.3; the outer coating layer is an enteric polymer that begins to dissolve in an aqueous media at a pH between about 6.8 to about 7.2; and wherein the incorporation of the bisacodyl into the dosage form is such that bisacodyl dissolves rapidly from the dosage form.

Preferably, the enteric polymer coating material has one inner enteric polymer coating layer and one outer enteric polymer coating layer.

The dosage forms of the present invention are to be distinguished from controlled (sustained) release compositions which slowly release a drug active over an extended period of time and extend the duration of drug action over that achieved with conventional delivery. The dosage forms of the present invention prevent the release of the drug active until the dosage form reaches the colon.

RAPIDLY DISSOLVING BISACODYL

The methods and compositions of the present invention comprise a safe and effective amount of rapidly dissolving bisacodyl. The phrase "safe and effective amount", as used herein, means an amount of rapidly dissolving bisacodyl high enough to provide a significant positive modification of the condition to be treated, but low enough to avoid serious side effects (at a reasonable benefit/risk ratio), within the scope of sound medical judgment. A safe and effective amount of rapidly dissolving bisacodyl will vary with the particular condition being treated, the age and physical condition of the patient being treated, the severity of the condition, the duration of the treatment, the nature of concurrent therapy and like factors. As indicated hereinabove, an effective dose of rapidly dissolving bisacodyl in compositions of the present invention is preferably substantially lower than the dose of bisacodyl required to achieve efficacy with conventional bisacodyl compositions.

A safe and effective dose of rapidly dissolving bisacodyl in the compositions of the present invention preferably provides from about 0.5 mg to about 15 mg of bisacodyl locally to the lumen of the lower gastrointestinal tract near the inlet of the small intestine to the colon or within the colon of a human patient. A preferred amount of bisacodyl dosed to a human patient is from about 0.75 mg to about 10 mg; more preferred is from about 1 mg to about 5 mg; more preferred still is from about 1 mg to about 4 mg; still more preferred is from about 2 mg to about 4 mg; also preferred is less than about 4 mg; also preferred is less than about 3 mg. The dosage unit form of the present invention preferably contains a single dose of bisacodyl in the above amounts.

As used herein, "rapidly dissolving bisacodyl" is bisacodyl in a physical form or composition which enhances the rate of dissolution of bisacodyl in the intestinal juices in the lumen of the colon compared to conventional bisacodyl formulations. For example the essentially complete dissolution of bisacodyl from the dosage forms of the present invention occurs within about 100 minutes, preferably within about 60 minutes, after substantially complete dissolution of the enteric coating in 0.2M pH 6.5 sodium phosphate buffer, with 0.5% sodium lauryl sulfate at a flow rate of 2 mL/minute in a 12 mm diameter flow through dissolution cell corresponding to USP apparatus 4. As used herein, "conventional bisacodyl formulations" are solid dosage forms of bisacodyl that do not disintegrate when in contact with an aqueous medium. Commercially-available bisacodyl compositions are typically coated with a low level of an enteric polymer or combination of polymers that is insoluble at pH's below about 6.5. An example of such a product is Dulcolax® (Boehringer Ingelheim Pharmaceuticals, Ridgefield, Conn.).

In the compositions of the present invention the rapidly dissolving bisacodyl is selected from the group consisting of micronized bisacodyl, inclusion complex of bisacodyl and a cyclodextrin, solid dispersion of bisacodyl on a hydrophilic substrate, and commercially available bisacodyl powder.

The micronized bisacodyl, inclusion complex of bisacodyl and a cyclodextrin, solid dispersion of bisacodyl on a hydrophilic substrate, and commercially available bisacodyl powder may be admixed with various other solid pharmaceutically acceptable excipients to enhance the dissolution rate of bisacodyl by promoting disintegration into primary drug particles to maximize surface area. Acceptable excipients include, but are not limited to, diluents (e.g., lactose, sucrose, glucose, starch, calcium sulfate, dicalcium phosphate, micro crystalline cellulose); binders (e.g., polyvinylpyrrolidone, pregelatinized starch, gelatin, hydroxypropyl methylcellulose, methylcellulose, hydroxyethyl cellulose, hydroxypropyl cellulose); lubricants (e.g., stearic acid, magnesium stearate); disintegrants (e.g., sodium starch glycolate, cross-linked polyvinylpyrrolidone, cross-linked carboxymethyl cellulose, pregelatinized starch); glidants (e.g., fumed silica); and buffers. Pharmaceutical excipients are disclosed in "Remington's Pharmaceutical Sciences", 17th Ed. (1985), pp. 1603–1644, which is herein incorporated by reference. The solids mixture may be prepared via a number of techniques well-known in the pharmaceutical sciences such as dry mixing, wet granulation, and fluid bed granulation, and be incorporated into a compressed, bi-convex tablet, using conventional equipment and processes.

A preferred rapidly dissolving bisacodyl of the present invention comprises micronized bisacodyl, optionally admixed with various solid excipients in order to promote disintegration of the drug from the substrate as primary drug particles to maximize bisacodyl dissolution. As used herein, "micronized bisacodyl", means solid bisacodyl which is finely divided. The particle size distribution of micronized bisacodyl is preferably such that greater than 90% of the particles are less than 10 $\mu$m in effective diameter, more preferably greater than 95% are less than 10 $\mu$m in effective diameter, more preferably still, greater than 99% are less than 10 $\mu$m in effective diameter. As used herein, "effective diameter" means the mean volume diameter, which is equivalent to the diameter of a sphere of equal volume to the particle being measured. Micronized bisacodyl, optionally admixed with various solid excipients, may be incorporated into the compressed, bi-convex tablet.

Another preferred rapidly dissolving bisacodyl is comprised of an inclusion complex of bisacodyl and a cyclodextrin, optionally admixed with various solid excipients in order to promote disintegration of the inclusion complex from the substrate as primary particles to maximize bisacodyl dissolution. As used herein, "cyclodextrin", means a cyclic carbohydrate molecule comprising six, seven, or eight glucose monomers arranged in a donut shaped ring which are termed α, β, and γ-cyclodextrin, respectively. See J. Pitha, L. Szente & J. Szejtli, "Molecular Encapsulation of Drugs by Cyclodextrins and Congeners", *Controlled Drug Delivery*, Vol. 1, S. D. Brunk, ed., CRC Press, Inc., Boca Raton, Fla., 1983, which is incorporated herein by reference. These molecules may also be modified by the addition of substituents such as hydroxypropyl groups to the hydroxyl groups of the glucose monomers on the outside of the ring. As used herein, "inclusion complex" means a complex between one or more bisacodyl molecules and one or more cyclodextrin molecules in which all or a portion of the bisacodyl molecule or molecules resides in the cavity or cavities of the cyclodextrin molecule or molecules without the formation of a covalent bond between the bisacodyl and cyclodextrin molecules. The molecular ratio of cyclodextrin to bisacodyl preferably ranges from about 0.5:1 to about 30:1 preferably from about 1:1 to about 10:1. Mixtures of cyclodextrins may also be used. Such complexes of cyclodextrin and bisacodyl may be prepared by any of a number of means well known to those skilled in the art, such as solubilization of bisacodyl in an aqueous solution of the cyclodextrin followed by spray drying or lyophilization of the resulting solution to produce a dry powder of the inclusion complex.

Cyclodextrin inclusion complexes of bisacodyl, optionally admixed with various solid excipients, may be incorporated into the compressed, bi-convex tablet.

Another preferred type of rapidly dissolving bisacodyl consists of a solid dispersion of bisacodyl on a hydrophilic substrate such as fumed silica and others known to one skilled in the art, optionally admixed with various solid excipients in order to promote disintegration of the solid dispersion from the substrate as primary particles to maximize bisacodyl dissolution. Typical ratios (weight:weight) of hydrophilic substrate to bisacodyl range from about 5:1 to about 20:1, preferably from about 8:1 to about 12:1. The solid dispersions may be prepared by mixing a solution of bisacodyl in a pharmaceutically suitable solvent such as acetone with the hydrophilic substrate followed by evaporation of the solvent using any number of processes well known to those skilled in the art.

Solid dispersions of bisacodyl on a hydrophilic substrate, optionally admixed with various solid excipients, may be incorporated into the compressed, bi-convex tablet.

A further preferred type of bisacodyl consists of commercially available bisacodyl powder, corresponding to USP specifications, admixed with various solid excipients in order to promote disintegration of the drug from the substrate as primary particles to maximize bisacodyl dissolution.

THE DOSAGE FORM AND NON-pH DEPENDENT SMOOTHING COAT

A safe and effective amount of rapidly dissolving bisacodyl is incorporated into a conventional, bi-convex, compressed tablet, with a maximum diameter of about 4 mm to about 10 mm. The conventional, bi-convex, compressed tablet is a tablet compressed by conventional processes, this tablet having a non-smooth surface with edges or sharp curves. However, the application of a safe and effective amount of a non-pH dependent smoothing coat to this tablet, will provide a smooth tablet surface, free from edges or sharp curves. This smoothing coat reshapes or rounds out the bi-convex tablet. In addition the application of the non-pH dependent smoothing coat to the bi-convex tablet can provide a spherical and/or elliptical tablet wherein the elliptical tablet has a ratio of the long to short diameters of no greater than about 1.5.

As used herein, "compressed, bi-convex tablet" means a conventional tablet, having a round face, prepared through the compression of a mixture of bisacodyl and pharmaceutical excipients, by two punches, preferably having an identical, spherical standard or deep-concave tooling. Especially preferred tooling is a deep-concave tooling of which the typical axis radius is 3.5 mm for a 5 mm face diameter. Another preferred tooling is a dual radius concave tooling having a smaller axis radius at the face of which the typical ratio is 1/3 to 1/3.5 versus the center axis radius. As indicated above this tablet has a non-smooth surface with edges or sharp curves.

As used herein, "elliptical" means an ellipsoid, a solid figure in which all plane surfaces are approximately ellipses or circles, described by the equation $x^2/a^2 + y^2/b^2 + z^2/c^2$, wherein $\leq 1.5$, and "a" is approximately between 4 mm and 10 mm.

As used herein, "smooth surface free from edges or sharp curves" means that, after the application of the smoothing coat, no edges or sharp curves exist on the dosage form sufficient to produce thin spots in the enteric coating relative to the mean enteric coating thickness. Especially preferred dosage forms are conventional tablet forms, having a round face, for example conventional sugar tablets, with a diameter of about 4 mm to about 8 mm; more preferably about 5 mm to about 7 mm. The non-pH dependent smoothing coat, applied to these tablets will provide a smooth tablet surface free from edges or sharp curves. After application of the smoothing coat, preferably all of the dosage forms are of a uniform size prior to coating with the enteric polymer coating material. Preferably the diameter of every tablet is within about 5%, more preferably within about 2%, of the mean diameter. The smooth surface and uniform size allow for uniform enteric coating thickness and therefore uniform dissolution of the enteric polymer coating material.

The non-pH dependent smoothing coat is any non-enteric polymer coating material or is any inert, water soluble polymer material, known to a skilled artisan. The non-pH dependent smoothing coat preferably is selected from the group consisting of sucrose, Arabic gum, hydroxypropyl cellulose, hydroxypropyl methylcellulose, polyethylene glycol, low viscosity hydroxypropyl cellulose, low viscosity hydroxypropyl methylcellulose, gelatin, sodium alginate, dextrin, psyllium husk powder, and mixtures thereof, more preferably the non-pH dependent smoothing coat is selected from the group consisting of sucrose, Arabic gum, low viscosity hydroxypropyl cellulose, low viscosity hydroxypropyl methylcellulose, gelatin, sodium alginate, dextrin, psyllium husk powder, and mixtures thereof, even more preferably the smoothing coat comprises a mixture of one or more of the above smoothing coat materials with a processing agent selected from the group consisting of talc, lactose, precipitated calcium carbonate, titanium dioxide, silica, microcrystalline cellulose and mixtures thereof, to effectively round or smooth out the compressed core tablet.

The level of the smoothing coat depends on the diameter of the tablet and the size and shape of the tooling used. Preferably the level of the smoothing coat is from about 10% to about 50%, more preferably from about 20% to about 40% of the core tablet weight, even more preferably from about 25% to about 35% of the core tablet weight.

The non-pH dependent smoothing coat may be applied to the compressed, bi-convex tablet by any number of processes well known to those skilled in the art, including, but not limited to, perforated pan coating and fluid bed coating.

The tablet preferably comprises a solid form of rapidly dissolving bisacodyl and is compressed using conventional equipment and processes. Any compressed tablet preferably is made such that it rapidly disintegrates in intestinal juices.

THE ENTERIC POLYMER COATING MATERIAL

In the compositions of the present invention, the polymer coating material prevents the release of bisacodyl as the dosage form passes through the upper gastrointestinal tract, including the mouth, esophagus, stomach, and small intestine, until the dosage form is near the junction between the small intestine and the colon or is in the colon. This precludes systemic absorption of bisacodyl and/or desacetyl bisacodyl from the upper gastrointestinal tract (and subsequent biliary excretion of metabolic conjugates), and/or dilution of the released bisacodyl in the contents of the upper gastrointestinal tract (which results in a less concentrated dose of the drug reaching the site of activity in the colon). Therefore, the dosage forms of the present invention provide a method of delivering bisacodyl in a concentrated and rapidly dissolving form to the colon. This results in effective laxation at a low dose of the drug with reduced absorption of bisacodyl and/or its metabolites which results in lower side effects such as secondary diarrhea produced by biliary excretion of metabolic conjugates.

As used herein, "enteric polymer coating material," refers to materials which completely surround and encase the bisacodyl in the unit dosage form prior to oral administration. The polymer coating material of the present invention does not contain any active compound, i.e. bisacodyl, of the present invention. In addition the present invention does not comprise enteric coated microcrystal spheres, enteric coated particles, or enteric coated granules of the active compound. Preferably, a substantial amount or all of the enteric polymer coating material is dissolved before the bisacodyl is released from the dosage form, so as to achieve rapid dissolution of the bisacodyl.

The polymer coating materials are selected such that rapidly dissolving bisacodyl will be released at about the time that the dosage form reaches the inlet between the small intestine and the colon, or thereafter in the colon. The selection is based upon the pH profile of the small intestine and colon. The pH of the small intestine gradually increases from about 5 to 5.5 in the duodenal bulb to about 7.2 in the distal portions of the small intestine (ileum). The pH drops significantly at the ileocecal junction to about 6.3 and very gradually increases to about 7 in the left or descending colon. In order to provide a predictable dissolution time corresponding to the small intestinal transit time of about 3 hours and permit reproducible release of drug at the inlet between the small intestine and the colon, or thereafter in the colon, the coating should begin to dissolve within the pH range of the small intestine and continue to dissolve at the pH of the proximal colon. This means that a single coating layer of a single enteric polymer coating material should begin to dissolve in the pH range of about 5 to 6.3, which requires a minimum coating thickness of 250 $\mu$m. (See P&G Copending Patent Application Case No. 5671, Ser. No. 08/442,915, Kelm, Manring, Davis, Dobrosi, Mandel and McCauley-Myers, filed on May 17, 1995 now abandoned). Single layer coatings of enteric polymer coating materials which begin to dissolve at higher pH levels, such as about 7, require less coating thickness for the dosage form to reach the inlet between the small intestine and the colon, or the colon. However, any coating remaining when the dosage form reaches the colon will not dissolve in the proximal portions of the colon where the pH is less than 7, thus delaying drug release until the dosage form has reached a portion of the colon where the lumenal pH is greater than 7.

In order to provide for release in the proximal colon while minimizing total enteric polymer coating thickness, the enteric polymer coating materials of the present invention consist of a sequential coating of multiple, preferably two, materials in distinct, multiple layers. The outer coating layer consists of an enteric polymer coating material which begins to dissolve at a pH between about 6.8 to about 7.2 in an amount such that this layer is completely dissolved when the dosage form is in the distal small intestine. The inner layer, or layers, consist(s) of enteric polymer coating material(s) that begin to dissolve at pHs between about 5 to about 6.3, preferably a pH between about 5 to about 6, more preferably a pH between about 5 to about 5.5. The amount(s) of the inner layer(s) is(are) such that release of the drug is delayed until the dosage form has reached the inlet between the small intestine and the colon, or the colon. Thus, the function of the outer coating layer of enteric polymer coating material is to prevent release of the drug from the stomach through to the distal portion of the small intestine, and the function of the inner coating layer(s) is to prevent release of the drug from the distal portion of the small intestine (from the time the outermost layer has dissolved) to the inlet between the small intestine and the colon, or the colon.

Preferred coating materials for the outer coating layer of enteric polymer coating material include pH-sensitive materials, which remain intact in the lower pH environs of the stomach and small intestine, but begin to dissolve in an aqueous solution at a pH between about 6.8 to about 7.2. The coating thickness is dependent upon the size of the unit dosage form, but ranges from about 20 $\mu$m to about 50 $\mu$m. Preferred materials for the outer coating layer of enteric polymer coating material are poly(methacrylic acid, methyl methacrylate) 1:2 (Eudragit® S) and mixtures of poly (methacrylic acid, methyl methacrylate) 1:1 (Eudragit® L) and poly(methacrylic acid, methyl methacrylate) 1:2 (Eudragit® S) in a ratio of about 1:10 to about 1:2, preferably about 1:5 to about 1:3. Especially preferred is Eudragit® S.

Eudragit® L, is an anionic copolymer derived from methacrylic acid and methyl methacrylate, with a ratio of free carboxyl groups to the ester groups of approximately 1:1, and a mean molecular weight of approximately 135,000, from Rohm Tech; Eudragit® S is an anionic copolymer derived from methacrylic acid and methyl methacrylate, with a ratio of free carboxyl groups to the ester groups of approximately 1:2, and a mean molecular weight of approximately 135,000, from Rohm Tech.

Preferred coating materials for the inner coating layer(s) include pH-sensitive materials, which remain intact in the lower pH environs of the stomach and small intestine, but which disintegrate or dissolve at the pHs commonly found in the distal portion of the small intestine and, especially, in the proximal colon. The inner coating layer polymers have a low apparent pKa range to minimize the impact of the drop in the pH across the ileo-cecal valve. The inner coating layer enteric polymer(s) begin to dissolve in an aqueous solution at a pH between about 5 to about 6.3. It is particularly important that the enteric polymer(s) be soluble in the proximal portions of the colon where the lumenal pH is typically lower than that in the distal portion of the small intestine. This lower pH is due to the presence of short chain fatty acids produced by the metabolic activity of bacteria residing in the colon.

The enteric polymer coating materials for the inner layer (s) are selected from the group consisting of cellulose acetate phthalate; cellulose acetate trimelliate; hydroxypropyl methylcellulose phthalate; hydroxypropyl methylcellulose acetate succinate; polyvinyl acetate phthalate; poly (methacrylic acid, methyl methacrylate) 1:1; poly (methacrylic acid, ethyl acrylate) 1:1; and compatible mixtures thereof, preferably poly(methacrylic acid, ethyl acrylate) 1:1; poly(methacrylic acid, methyl methacrylate) 1:1, and compatible mixtures thereof, more preferably poly (methacrylic acid, ethyl acrylate) 1:1.

Specific examples of these polymer coating materials include the following:

Eudragit® L, an anionic copolymer derived from methacrylic acid and methyl methacrylate, with a ratio of free carboxyl groups to the ester groups of approximately 1:1, and a mean molecular weight of approximately 135,000;

Eudragit® L 30 D, an aqueous acrylic resin dispersion, an anionic copolymer derived from methacrylic acid an ethyl acrylate with a ratio of free carboxyl groups to the ester groups of approximately 1:1, and a mean molecular weight of approximately 250,000; (it is supplied as an aqueous dispersion containing 30% w/w of dry lacquer substance);

Eudragit® L 100-55, an anionic copolymer derived from methacrylic acid and ethyl acrylate, with a ratio of free carboxyl groups to the ester groups of approximately 1:1, and a mean molecular weight greater than about 100,000;

cellulose acetate phthalate or CAP®, available from Eastman Chemical; cellulose acetate trimelliate, CAT® available from Eastman Chemical; hydroxypropyl methylcellulose phthalate (USP/NF type 220824) HPMCP 50® and (USP/NF type 200731) HPMCP 55® available from Shin Etsu Chemical; polyvinyl acetate phthalate, PVAP®, available from Colorcon; hydroxypropyl methylcellulose acetate succinate, HPMCAS®, available from Shin Etsu Chemical.

A preferred polymer coating material is poly(methacrylic acid, ethyl acrylate) 1:1 (Eudragit® L 100-55), wherein for diameters of about 4 to about 7 mm, the preferred coating thickness is about 120 to 350 μm, and about 100 to 300 μm, respectively.

Another preferred polymer is poly(methacrylic acid, methyl methacrylate) 1:1 (Eudragit® L), wherein for diameters of about 4 to about 7 mm, the preferred coating thicknesses is about 110 to 300 μm and about 90 to 250 μm, respectively.

The total amount of enteric polymer coatings on the dosage form must be sufficient such that complete dissolution of the coating does not occur until the dosage form is at a location within the gastrointestinal tract near the opening to, or within the colon, thereby releasing bisacodyl in the colon. This necessitates the requirement of a rounded, spherical or elliptical dosage form free from surface edges or sharp curves which will produce thin spots in the coating. The coating over such thin spots will dissolve prior to the dosage form reaching the colon, resulting in premature release of bisacodyl.

Transit of pharmaceutical dosage forms through the gastrointestinal tract has been characterized in the literature (i.e., M. Ashford and J. T. Fell, *J. Drug Targeting*, 1994, Vol. 2, pp. 241–258). Gastric emptying of pharmaceutical dosage forms can be highly variable, but transit through the small intestine is relatively constant with a mean transit time of about three hours. The pH—solubility behavior of the enteric polymers of the present invention is such that significant dissolution of the enteric polymer coating will not occur until the dosage form has emptied from the stomach, thereby eliminating the variability of gastric emptying as a factor in determining the amount of coating required to achieve release of bisacodyl in the colon. Therefore, the amount of enteric polymer coating should be such that it is substantially dissolved during the approximate three hour transit time of the small intestine.

Dissolution of the enteric polymers of the present invention is influenced by the size of the dosage form, and the pH, ionic strength, and velocity of the surrounding aqueous medium. The latter three factors vary throughout the length of the small intestine and colon. In addition, the effect of these factors upon dissolution rate varies with each enteric polymer. However, the amount of a single coating layer of enteric polymer is substantial, wherein the enteric polymer is soluble in the proximal portions of the colon, as taught in P&G Copending Patent Application Case No. 5671, Ser. No. 08/442,915, Kelm, Manring, Davis, Dobrosi, Mandel and McCauley-Myers, filed on May 17, 1995 now abandoned. An important aspect of the present invention is the use of multiple coating layers of enteric polymers in which the outermost layer consists of an enteric polymer or combination of enteric polymers which are insoluble below about pH 6.8. The inner layer(s) consist of enteric polymer(s) that begin to dissolve at a pH between about 5 to about 6.3 in order to be soluble in the proximal portions of the colon. The use of multiple layers in the manner described herein reduces the total amount of enteric polymer coating relative to the use of a single coating layer of enteric polymer that is soluble in the proximal portions of the colon.

The more important parameters for determination of the amount of enteric polymer required to delay drug release until the dosage form has reached the colon have been found to include the pH solubility profiles of the enteric polymers employed in the outermost and inner coating layers and the size of the dosage form. Approximate minimum amounts of enteric polymer as a function of the pH at which the polymer begins to dissolve and dosage form size are shown in the following table, Table 1. Also included are examples of enteric polymers.

TABLE 1

| Diameter (mm) | Layer | pH | Minimum Thickness (μm) | Example Enteric Polymers |
|---|---|---|---|---|
| 3 | Inner | 5.0 | 150 | HPMCP 50 |
| 3 | Outer | 7.0 | 40 | Eudragit ® S |
| 5 | Inner | 5.0 | 130 | HPMCP 50 |
| 5 | Outer | 7.0 | 30 | Eudragit ® S |
| 10 | Inner | 5.0 | 100 | HPMCP 50 |
| 10 | Outer | 7.0 | 20 | Eudragit ® S |
| 3 | Inner | 5.5 | 140 | Eudragit ® L100-55 |
| 3 | Outer | 7.0 | 40 | Eudragit ® S |
| 5 | Inner | 5.5 | 120 | Eudragit ® L100-55 |
| 5 | Outer | 7.0 | 30 | Eudragit ® S |
| 10 | Inner | 5.5 | 90 | Eudragit ® L100-55 |
| 10 | Outer | 7.0 | 20 | Eudragit ® S |
| 3 | Inner | 6.0 | 130 | Eudragit ® L |
| 3 | Outer | 7.0 | 40 | Eudragit ® S |
| 5 | Inner | 6.0 | 110 | Eudragit ® L |
| 5 | Outer | 7.0 | 30 | Eudragit ® S |
| 10 | Inner | 6.0 | 80 | Eudragit ® L |
| 10 | Outer | 7.0 | 20 | Eudragit ® S |

The enteric polymer coating material may by applied to the rounded, spherical or elliptical substrate as a solution in a pharmaceutically acceptable solvent such as ethanol, acetone, isopropanol, ethyl acetate, or mixtures thereof; as an aqueous solution buffered with ammonium hydroxide; or as a fine dispersion in water using any number of processes known to one skilled in the art, including but not limited to, perforated pan coating and fluid bed coating.

To enhance the elasticity of the coating materials, preferably the coating material of the present invention also comprises a plasticizer. Appropriate plasticizers include polyethylene glycols, propylene glycols, dibutyl phthalate, diethyl phthalate, tributyl citrate, tributyrin, butyl phthalyl butyl glycolate (Santicizer® B-16, from Monsanto, St. Louis, Mo.), triacetin, castor oil and citric acid esters; preferably the plasticizer is dibutyl phthalate or triethyl citrate. These plasticizers are present in an amount to facilitate the coating process and to obtain an even coating film with enhanced physical stability. Generally the coating material comprises from about 0% to about 50% of a plasticizer, preferably from about 0% to about 25%, more preferably about 10% to about 20% by weight of the polymer.

In addition, to facilitate the coating process, the enteric polymer coating material may also comprise inert solid particulates. Preferred inert solid particulates include talc and titanium dioxide.

For the enteric polymer materials, the selections of optional plasticizer, optional inert solid particulate, and levels thereof, coating formulation type (solvent, ammoniated aqueous solution, or aqueous dispersion), and process of coating are based upon the specific enteric polymer used and the type of dosage form used according to criteria known to those skilled in the art.

OPTIONAL INGREDIENTS

The compositions of the present inventions can optionally include active drug ingredients in addition to bisacodyl. Non-limiting examples of other active drug agents and amounts typically present in such compositions include the following: docusate sodium, calcium or potassium, from about 5 mg to about 500 mg, preferably from about 50 mg to about 250 mg; glycyrrhiza extract comprising from about 5% to about 30%, preferably from about 10% to about 16%, glycyrrhizic acid, from about 2 mg to about 200 mg, preferably from about 20 mg to about 100 mg; aloe, from about 50 mg to about 500 mg, preferably from about 195 mg to about 325 mg; peppermint oil, from about 250 mg to about 4000 mg, preferably from about 500 mg to about 2500 mg; poloxamer 188, from about 10 mg to about 500 mg, preferably from about 100 mg to about 250 mg; ginger, from about 650 mg to about 1300 mg; mineral oil, USP, from about 500 mg to about 40 g; preferably from about 800 mg to about 20 g; castor oil, USP, from about 500 mg to about 60 g; preferably from about 1 g to about 45 g; and magnesium hydroxide, from about 500 mg to about 5 g, preferably from about 1 g to about 2.8 g.

METHOD OF USE

Another aspect of the present invention is methods for providing laxation for humans and lower animals in need thereof by peroral administration of the above-described dosage form and compositions. Conditions for which such laxation may beneficially be provided include the following: constipation, adjunctive therapy for irritable bowel syndrome, and bowel cleansing prior to diagnostic or surgical procedures.

An advantage of providing bisacodyl to patients using the present compositions is that laxation benefits are generally achieved without the secondary diarrhea commonly associated with conventional bisacodyl compositions. Another advantage is that such laxation benefits are often achieved more quickly than with conventional bisacodyl compositions.

Compositions and dosage forms of the present invention described hereinabove are preferably administered when laxation is needed. One dose is often sufficient to provide the needed laxation, but several dosages can be used sequentially when needed. Such sequential doses are preferably provided to a patient from about 8 hours to about 24 hours apart, up to a maximum of about 4 dosages.

METHOD OF MAKING

Enteric polymers are generally applied onto the rounded, spherical or elliptical tablets as solutions in organic solvents. The solvents commonly employed as vehicles are methylene chloride, ethanol, methanol, isopropyl alcohol, acetone, ethyl acetate and combinations thereof. The choice of the solvent is based primarily on the solubility of the polymer, ease of evaporation, and viscosity of the solution.

Some polymers are also available in aqueous systems. Currently, three aqueous enteric polymer coatings are available for commercial use in the United States. These are Eudragit® L30D (methacrylic acid-ethyl acrylate copolymer marketed by Rohm-Haas GmBH, West Germany); Aquateric® (cellulose acetate phthalate-containing product marketed by FMC Corporation, Philadelphia, Pa.); and Coateric® (a polyvinyl acetate phthalate based product marketed by Colorcon, Inc., West Point, Pa.). Unlike organic solutions, these aqueous-based systems can be prepared at high concentration without encountering high viscosity. Also, these aqueous systems do not have the problems associated with the organic systems such as flammability, toxicity of the residual solvent in the dosage form, etc.

Coating can be achieved by methods known to one skilled in the art such as by using fluidized bed equipment, perforated pans, a regular pharmaceutical pan, compression coating, etc. by continuous or short spray methods, or by drenching.

All percentages used herein are by weight of the composition unless otherwise indicated.

The following non-limiting examples provide typical formulations for compositions and dosage forms of the present invention, and typical methods for treating human disorders with such compositions.

EXAMPLE 1

A dosage form of the following formulation is prepared as described below:

| Substrate | | Non-pH Dependent Smoothing | |
|---|---|---|---|
| Component | Wt. (mg) | Component | Wt. (mg) |
| Bisacodyl | 4 | Sucrose | 10 |
| Lactose | 34 | Talc | 6 |
| Corn Starch | 8 | Arabic gum | 1 |
| Pre-gelatinized Starch | 12 | | |
| HPC-L[1] | 1.7 | | |
| Magnesium Stearate | 0.3 | | |
| Inner Enteric Coat | | Outermost Enteric Coat | |
| Component | Wt (mg) | Component | Wt. (mg) |
| Eudragit ® L30D[2] | 31 | Eudragit ® S100[3] | 2.8 |
| TEC[4] | 2.4 | TEC[4] | 1.4 |
| Talc, USP | 5 | | |
| | | Talc, USP | 0.9 |

| Colored Sugar Coat Component | Wt. (mg) |
|---|---|
| Sucrose | 9.5 |
| Talc | 3 |
| Arabic gum | 0.4 |
| FD&C Red No. 3 | 0.01 |

[1]Hydroxypropyl Cellulose, Low-substituted, Dow Chemical.
[2]30% w/w suspension of methacrylic acid-ethyl acrylate copolymer, Eudragit ® L30D, Rohm Tech.
[3]Poly(methacrylic acid, methyl methacrylate) 1:2, Eudragit ® S100, Rohm Tech.
[4]Triethyl citrate.

Substrate

Bisacodyl, USP, Lactose, Corn Starch, Pre-gelatinized Starch and HPC-L are mixed and wet-granulated by a fluid-bed granulator. Then, the granules are blended with magnesium stearate in a V-blender and compressed into bi-convex tablet with 5-mm diameter.

Non-pH Dependent Smoothing Coat

Arabic gum is dissolved in warm purified water and sucrose is dissolved in this solution. Then, talc is suspended in this Arabic-gum/sucrose solution to produce a 74% by weight syrup which is coated on the substrates described above in either a perforated pan coater or conventional pan coater maintaining an outlet air/bed temperature of about 45° C.

Inner Enteric Coat

Eudragit® L30D is dissolved in purified water. Separately, talc and TEC are suspended/dissolved in water. Then, these two are combined to a uniform suspension. The resulting mixture is coated onto the inner sugar-coated substrates above in a perforated pan coater maintaining an outlet air/bed temperature of about 35° C.

Outermost Enteric Coat

Eudragit® S100 is dispersed in water containing about 0.2% of ammonia and then TEC is dissolved in the suspension. Separately, talc is suspended in water and combined to the Eudragit/TEC suspension. The resulting mixture is coated onto the inner enteric coated substrates above in a perforated pan coater maintaining an outlet air/bed temperature of about 35° C.

Colored Sugar Coating

Arabic gum is dissolved in warm purified water and sucrose is dissolved in this solution. Separately, FD&C Red No. 3 is dissolved in water and then mixed with the Arabic-gum/sugar solution. Then, talc is suspended in this colored Arabic-gum/sucrose solution to produce a 74% by weight syrup. The resulting mixture is coated on the substrates described above in either a perforated pan coater or conventional pan coater maintaining an outlet air/bed temperature of about 45° C. The color-coated substrates are then polished with proper wax such as Carnauba wax, white bees wax, or a pre-mixed wax solution (Opagross 6000, Colorcon) in either a perforated pan coater or conventional pan coater.

Example 2

A dosage form of the following formulation is prepared as described below:

| Substrate | | Non-pH Dependent Smoothing | |
|---|---|---|---|
| Component | Wt. (mg) | Component | Wt. (mg) |
| Bisacodyl | 4 | Polyethylene Glycol 6000 | 11 |
| Lactose | 34 | Talc | 7 |
| Corn Starch | 8 | | |
| Pre-gelatinized Starch | 12 | | |
| HPC-L[1] | 1.7 | | |
| Magnesium Stearate | 0.3 | | |
| Inner Enteric Coat | | Outermost Enteric Coat | |
| Component | Wt. (mg) | Component | Wt. (mg) |
| Eudragit ® L100-55[2] | 18 | Eudragit ® S100[3] | 5 |
| Dibutyl Phthalate | 4 | Dibutyl Phthalate | 1 |
| Talc, USP | 8 | Red Ferric Oxide | 1 |
| | | Talc, USP | 2 |

[1]Hydroxypropyl Cellulose, Low-substituted, Dow Chemical.
[2]Poly(methacrylic acid, ethyl acrylate) 1:1, Eudragit ® L100-55, Rohm Tech.
[3]Poly(methacrylic acid, methyl methacrylate) 1:2, Eudragit ® S100, Rohm Tech.

Substrate

Bisacodyl, USP, Lactose, Corn Starch, Pre-gelatinized Starch and HPC-L are mixed and wet-granulated by a fluid-bed granulator. Then, the granules are blended with magnesium stearate in a V-blender and compressed into a bi-convex tablet with 5-mm diameter.

Non-pH Dependent Smoothing Coat

Polyethylene Glycol 6000(PEG 6000) is dissolved in purified water and then talc is suspended in this PEG 6000 solution to produce a 22% by weight suspension which is coated on the substrates described above in a perforated pan coater maintaining an outlet air/bed temperature of about 40° to 45° C.

Inner Enteric Coat

Eudragit® L100-55 and dibutyl phthalate are dissolved in a solution of isopropanol, acetone, and water (37:9:1) at levels of 8.0% and 1.6% (total weight percent), respectively. Talc is then suspended in the solution at a level of 3.3% by weight. The resulting mixture is coated onto the substrates above in a perforated pan coater maintaining an outlet air/bed temperature of about 30° C.

Outermost Enteric Coat

Eudragit® S and dibutyl phthalate are dissolved in a solution of isopropanol, acetone, and water (37:9:1) at levels of 8.0% and 1.6% (total weight percent), respectively. Red ferric oxide and talc are then suspended in the solution at levels of 1.2% and 2.1% by weight, respectively. The resulting mixture is coated onto the substrates above in a perforated pan coater maintaining an outlet air/bed temperature of about 30° C.

While particular embodiments of the present invention have been described, it will be obvious to those skilled in the art that various changes and modifications of the present invention can be made without departing from the spirit and scope of the invention. It is intended to cover, in the appended claims, all such modifications that are within the scope of this invention.

What is claimed is:

1. A compressed, bi-covex tablet for peroral administration in a human or other animal, having a gastrointestinal tract comprising a small intestine and a colon with a lumen therethrough having an inlet to the colon from the small intestine comprising:

a. a safe and effective amount of rapidly dissolving bisacodyl and pharmaceutically acceptable excipients necessary to form a compressed, bi-convex tablet, with a maximum diameter of about 4 mm to about 10 mm;

b. a non-pH dependent smoothing coat applied to the tablet to provide a smooth tablet surface free from edges and sharp curves; wherein the smoothing coat is selected from the group consisting of sucrose, Arabic gums hydroxypropyl cellulose, hydroxypropyl methylcellulose, polyethylene glycol, low viscosity hydroxypropyl cellulose, low viscosity hydroxypropyl methylcellulose, gelatin, sodium alginate, dextrin, psyllium husk powder, and mixtures thereof; and thereafter coating the tablet with:

c. at least one inner enteric polymer coating layer selected from the group consisting of cellulose acetate phthalate; cellulose acetate trimelliate; hydroxypropyl methylcellulose phthalate; hydroxypropyl methylcellulose acetate succinate; polyvinyl acetate phthalate; poly (methacrylic acid, methyl methacrylate) 1:1; poly (methacrylic acid, ethyl acrylate) 1:1; and compatible mixtures thereof, and d. an outer enteric polymer coating layer wherein the outer coating layer is an enteric polymer that begins to dissolve in an aqueous media at a pH between about 6.8 to about 7.2 selected from the group consisting of poly(methacrylic acid, methyl methacrylate) 1:2, and a mixture of poly(methacrylic acid, methyl methacrylate)

1.1 and poly(methacrylic acid, methyl methacrylate) 1:2 in a ratio of about 1:10 to about 1:2;

wherein the rapidly dissolving bisacodyl is released at a point near the inlet to, or within the colon; each of the inner coating layer(s) is an enteric polymer that begins to dissolve in an aqueous media at a pH between about 5 to about 6.3.

2. The composition of claim 1 wherein the rapidly dissolving bisacodyl is selected from the group consisting of micronized bisacodyl, an inclusion complex of bisacodyl and a cyclodextrin, a solid dispersion of bisacodyl on a hydrophilic substrate, and commercially available bisacodyl powder.

3. The composition of claim 1 wherein the rapidly dissolving bisacodyl also comprises a pharmaceutically acceptable excipient selected from the group consisting of diluents, binders, lubricants, disintegrants, glidants, buffers, and mixtures thereof, to enhance the dissolution rate of bisacodyl by promoting disintegration into primary drug particles to maximize surface area.

4. The composition of claim 1 wherein the rapidly dissolving bisacodyl is micronized bisacodyl.

5. The composition of claim 2 wherein the non-pH dependent smoothing coat is selected from the group consisting of sucrose, Arabic gum, low viscosity hydroxypropyl cellulose, low viscosity hydroxypropyl methylcellulose, gelatin, sodium alginate, dextrin, psyllium husk powder, and mixtures thereof.

6. The composition of claim 5 wherein the smoothing coat additionally comprises a processing agent selected from the group consisting of talc, lactose, precipitated calcium carbonate, titanium dioxide, silica, microcrystalline cellulose and mixtures thereof, to effectively round or smooth out the compressed core tablet.

7. The composition of claim 2 wherein the level of smoothing coat is from about 10% to about 50% of the core tablet weight.

8. The composition of claim 7 wherein the level of smoothing coat is from about 20% to about 40% of the core tablet weight.

9. The composition of claim 2 wherein the enteric polymer coating material comprises one inner coating layer.

10. The composition of claim 9 wherein the inner coating layer is selected from the group consisting of poly (methacrylic acid, methyl methacrylate) 1:1; poly (methacrylic acid, ethyl acrylate) 1:1; and compatible mixtures thereof.

11. The composition of claim 10 wherein the inner coating layer is poly(methacrylic acid, ethyl acrylate) 1:1, which has a coating thickness of about 120 μm to about 350 μm when the diameter is about 4 mm.

12. The composition of claim 10 wherein the inner coating layer is poly(methacrylic acid, ethyl acrylate) 1:1, which has a coating thickness of about 100 μm to about 300 μm when the diameter is about 7 mm.

13. The composition of claim 10 wherein the inner coating layer is poly(methacrylic acid, methyl methacrylate) 1:1, which has a coating thickness of about 110 μm to about 300 μm when the diameter is about 4 mm.

14. The composition of claim 10 wherein the inner coating layer is poly(methacrylic acid, methyl methacrylate) 1:1, which has a coating thickness of about 90 μm to about 250 μm when the diameter is about 7 mm.

15. The composition of claim 9 wherein the outer coating layer is poly(methacrylic acid, methyl methacrylate) 1:2.

16. The composition of claim 15 wherein the outer coating layer has a coating thickness of about 20 μm to about 50 μm.

17. A method for providing laxation in the colon of a human or lower animal by administering a safe and effective amount of the composition of claim 1 perorally.

* * * * *